United States Patent [19]
Patel et al.

[11] Patent Number: 5,872,128
[45] Date of Patent: Feb. 16, 1999

[54] STABILIZED COMPOSITION OF TICLOPIDINE HYDROCHLORIDE

[75] Inventors: Mahendra Patel, East Brunswick; Mukteeshwar Gande, Cranbury; Pankaj Dave, Kendall Park; Madhava Reddy Uppugalla, North Brunswick, all of N.J.

[73] Assignee: Invamed, Inc., Dayton, N.J.

[21] Appl. No.: 950,822

[22] Filed: Oct. 15, 1997

[51] Int. Cl.⁶ .................. C07D 513/04; A61K 31/435
[52] U.S. Cl. .............................. 514/301; 546/114
[58] Field of Search .............................. 546/114; 514/301

[56] References Cited

U.S. PATENT DOCUMENTS

| | | | |
|---|---|---|---|
| 4,051,141 | 9/1977 | Castaigne | 260/294.8 |
| 4,591,592 | 5/1986 | Chowhan | 514/301 |
| 5,382,577 | 1/1995 | Odawara et al. | 514/211 |
| 5,520,928 | 5/1996 | Sherman | 424/464 |

OTHER PUBLICATIONS

Physicians' Desk Reference—Edition 48, 1994, pp. 2370–2372, TICLID® entry for SYNTEX.

*Primary Examiner*—Zinna Northington Davis
*Attorney, Agent, or Firm*—Plevy & Associates

[57] ABSTRACT

A novel pharmaceutical composition including thienopyridine derivatives, primarily ticlopidine hydrochloride, having no other organic or inorganic acid stabilizing agents or metal stearates. The stable pharmaceutical composition also includes hydrogenated vegetable oil as lubricant and other suitable non-ionic inert pharmaceutical excipients.

17 Claims, No Drawings

STABILIZED COMPOSITION OF TICLOPIDINE HYDROCHLORIDE

FIELD OF INVENTION

This invention relates to stabilization of a pharmaceutical composition containing ticlopidine hydrochloride and other non-ionic inert excipients. Hydrogenated vegetable oil serves as an inert lubricant in the pharmaceutical composition.

BACKGROUND OF THE INVENTION

Ticlopidine hydrochloride is a platelet aggregation inhibitor. When taken orally, ticlopidine hydrochloride causes a time and dose-dependent inhibition of both platelet aggregation and release of platelet granule constituents, as well as prolongation of bleeding time. Ticlopidine hydrochloride is marketed by Syntex under the trade name TICLID®. Detailed information on TICLID® is available in the Physicians' Desk Reference.

In order for ticlopidine hydrochloride, with or without diluents, to be made into solid dosage forms, tablets for example, with pressure, using available equipment, it is necessary that the ticlopidine hydrochloride, either in crystalline or powdered form, possess a number of physical characteristics.

These characteristics include cohesiveness, lubrication and the ability to flow freely. Since, most materials have none or only some of these properties, methods or formulations have been developed to impart these desirable characteristics to medicinal substances sought to be compressed into tablets.

The additional ingredients added to medicinal substances, to impart these desirable characteristics, are termed "excipients." Examples of excipients include diluents, binders, and lubricants.

The compressed tablets are also required to be stable through their shelf life. However, the addition of certain excipients can adversely effect other characteristics of the compressed tablets, including shelf life, and size.

U.S. Pat. No. 4,051,141 discloses a thieno-pyridine derived drug designated ticlopidine hydrochloride. However, it is subject to discoloration during normal storage. The discoloration has been associated with degradation of the ticlopidine. The initiating factor of the ticlopidine degradation was adjudged to be the presence of certain excipients such as gelatin, povidone and magnesium stearate.

U.S. Pat. No. 4,591,592 discloses that compositions containing ticlopidine hydrochloride can be stabilized by the addition of acidic compounds. However, the use of an acid as a stabilizer, in addition to the use of magnesium stearate as a lubricant, makes the composition more complex than desirable. However, use of magnesium stearate accelerates the decomposition of ticlopidine hydrochloride. Additionally, although the composition disclosed within U.S. Pat. No. 4,591,592 is more stable than that of U.S. Pat. No. 4,051,141, it is still less stable than desirable.

U.S. Pat. No. 5,520,928 discloses a pharmaceutical composition comprising an active ingredient with another acidic compound stearic acid, and other suitable pharmaceutical excipients, and which does not contain any organic acid other than stearic acid. The stabilization is achieved using stearic acid, which also serves as the lubricant. However, a tablet containing ticlopidine hydrochloride 250, microcrystalline cellulose 130, stearic acid 9.4 and croscarmellose sodium 0.6 mg, has a weight of 390 mg per tablet. Additionally, the typical composition has stearic acid as a stabilizer and croscarmellose sodium as a disintegrant, which also results in a composition more complex than desirable.

It is therefore an object of the invention to have a novel pharmaceutical composition with a fewer number of ingredients, without diluent, and with a smaller compressed tablet weight of 300 mg per 250 mg of ticlopidine hydrochloride.

It is a further object of the invention to have a stable pharmaceutical composition for ticlopidine hydrochloride containing no acid stabilizing agent alone or in combination with lubricant magnesium stearate.

And, it is yet a further object of the invention to have a pharmaceutical composition ticlopidine hydrochloride which uses hydrogenated vegetable oil as a lubricant, hydroxypropyl cellulose as a binder and corn starch as a disintegrant, all of which are substantially free of an effective amount of organic acid.

SUMMARY OF THE INVENTION

A pharmaceutical composition comprising a therapeutically effective amount of an active ingredient, and a lubricant, wherein said active agent is ticlopidine hydrochloride, and said lubricant is hydrogenated vegetable oil.

DETAILED DESCRIPTION OF THE INVENTION

The present invention discloses a pharmaceutical composition comprising of an active ingredient with a fewer number of inactives than previously seen. The composition is without any diluent, and can be compressed into a tablet, which is within the pharmaceutically acceptable stable dosage form, having a relatively small size.

The invention contains no acid stabilizing agent, no metal stearate lubricants, no ionic disintegrants, and is substantially free of an effective amount of organic acid. The invention can be practiced in the form of a tablet or capsule comprising of ticlopidine hydrochloride, hydrogenated vegetable oil as the lubricant, hydroxypropyl cellulose as the binder and corn starch as the disintegrant.

The invention is further illustrated by the following further example, which is not intended to limit the scope of the invention, but is given by way of illustration.

EXAMPLE

A manufacturing process comprising of initially mixing ticlopidine hydrochloride (83.3%) with hydroxypropyl cellulose (11%) and corn starch (3%) and then aqueous granulation. The dried granulation is screened through suitable mill to get a desired particle size. The milled granules are lubricated using hydrogenated vegetable oil. The final-blend granules either can be compressed into tablets or filled into capsules.

| Ingredients | Grams per 1000 Tablets |
| --- | --- |
| Ticlopidine Hydrochloride | 250 |
| Hydroxypropyl Cellulose | 33 |
| Corn Starch | 9 |
| Hydrogenated Vegetable Oil | 8 |
| Total Weight | 300 |
| Purified Water | about 130 mL |

Tablets are prepared as follows: Ticlopidine hydrochloride, hydroxypropyl cellulose and corn starch are mixed in a suitable mixer. Purified water is added slowly with continuous mixing. The resultant wet granulation is dried at approximately 60° C. to moisture content of approximately 3%. The dried granules are milled and blended with the hydrogenated vegetable oil. The final-blend is compressed into tablets at an average weight of approximately 300 mg. As a final step the tablets are given an appropriate coating.

The finished product were stored at room temperature RT (25°–30° C.) and accelerated stability condition AST (40° C./75% RH) for 1 month, 2 months and 3 months. All samples were analyzed for the presence of a compound known to result from the decomposition of ticlopidine hydrochloride. No change was found in the impurity level indicating that the novel pharmaceutical composition is suitably stable.

|         |              |              |
| ------- | ------------ | ------------ |
| Initial | 0.02%        |              |
| 1 month | 0.02% (RT)   | 0.02% (AST)  |
| 2 months| 0.02% (RT)   | 0.02% (AST)  |
| 3 months| 0.02% (RT)   | 0.02% (AST)  |

Although the invention has been described in a preferred form with a certain degree of particularity, it is understood that the present disclosure of the preferred form has been made only by way of example, and that numerous changes in the details of construction and combination and arrangement of procedures and parts may be made without departing from the spirit and scope of the invention as hereinafter claimed. It is intended that the patent shall cover by suitable expression in the appended claims, whatever features of patentable novelty exist in the invention disclosed.

We claim:

1. A pharmaceutical composition in solid dosage form for inhibiting platelet aggregation consisting essentially of an effective amount of a mixture of:

an active ingredient consisting essentially of ticlopidine hydrochloride;

a pharmaceutically acceptable lubricant consisting essentially of hydrogenated vegetable oil; and a pharmaceutically acceptable disintegrant consisting essentially of corn starch, wherein the composition is stable for at least three months at ambient temperature.

2. The composition of claim 1, further comprising:

a binder consisting essentially of hydroxypropylcellulose.

3. The composition of claim 1, wherein said active ingredient is present in an amount of approximately 65% to approximately 90% by weight.

4. The composition of claim 1, wherein said lubricant is present in an amount of approximately 0.2% to approximately 10% by weight.

5. The composition of claim 2, wherein said disintegrant is present in an amount of approximately 2% to approximately 15% by weight.

6. The composition of claim 2, wherein said binder is present in an amount of approximately 5% to approximately 15% by weight.

7. The composition of claim 1, wherein said composition is substantially free of an effective amount of organic acid.

8. The composition of claim 1, wherein said composition is substantially free of metal stearates.

9. The composition of claim 1, wherein said composition is in the form of a tablet having a weight of approximately 280 mg to approximately 450 mg, per 250 mg of ticlopidine hydrochloride.

10. A pharmaceutical composition in solid dosage form for inhibiting platelet aggregation consisting essentially of an effective amount of a mixture of:

approximately 65% to 90% by weight of an active ingredient consisting essentially of ticlopidine hydrochloride;

approximately 0.2% to 10% by weight of a pharmaceutically acceptable lubricant consisting essentially of hydrogenated vegetable oil;

approximately 2% to 15% by weight of a pharmaceutically acceptable disintegrant consisting essentially of corn starch; and approximately 5% to 15% by weight of a binder, wherein the composition is stable for at least three months at ambient temperature.

11. The composition of claim 10, wherein said composition is substantially free of an effective amount of organic acid.

12. The composition of claim 10, wherein said composition is substantially free of metal stearates.

13. The composition of claim 10, wherein said binder consists essentially of hydroxypropyl cellulose.

14. The composition of claim 10, wherein said composition is in the form of a tablet having a weight of approximately 280 mg to approximately 450 mg per 250 mg of ticlopidine hydrochloride.

15. A method for producing a pharmaceutical composition in solid dosage form for inhibiting platelet aggregation, comprising the steps of:

mixing an effective amount of an active ingredient consisting essentially of ticlopidine hydrochloride, a pharmaceutically acceptable lubricant consisting essentially of hydrogenated vegetable oil, and a pharmaceutically acceptable disintegrant consisting essentially of corn starch in a suitable mixer;

adding purified water to the mixture with continuous mixing;

drying the mixture at approximately 60° C. to a moisture content of approximately 3%;

milling and blending the dried mixture with hydrogenated vegetable oil;

compressing the dried, milled, and blended mixture into compressed tablets; and applying an appropriate coating to the compressed tablets, wherein said composition is stable for at least three months at ambient temperature.

16. The method of claim 15, wherein said compressed tablets are approximately 300 mg.

17. The method of claim 15, wherein said compressed tablets are approximate 280 mg to approximately 450 mg, per 250 mg of ticlopidine hydrochloride.

* * * * *